US010894886B2

(12) United States Patent
Gupta et al.

(10) Patent No.: US 10,894,886 B2
(45) Date of Patent: *Jan. 19, 2021

(54) COATING SYSTEM

(71) Applicant: Elementis Specialties, Inc., East Windsor, NJ (US)

(72) Inventors: Rajni Gupta, Princeton, NJ (US); Wouter Ijdo, Yardley, PA (US); Yanhui Chen, Princeton, NJ (US); Prashant Deshmukh, Plainsboro, NJ (US); James A. Heck, Robbinsville, NJ (US); Wayne Hoyte, Parlin, NJ (US); Maurice Gray, Saint Albans, NY (US)

(73) Assignee: Elementis Specialties, Inc., East Windsor, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/007,225

(22) Filed: Jun. 13, 2018

(65) Prior Publication Data

US 2018/0355185 A1 Dec. 13, 2018

Related U.S. Application Data

(60) Provisional application No. 62/518,791, filed on Jun. 13, 2017.

(51) Int. Cl.
| | |
|---|---|
| *C09D 4/06* | (2006.01) |
| *C09D 7/20* | (2018.01) |
| *C08G 63/21* | (2006.01) |
| *C08J 3/24* | (2006.01) |
| *C09D 167/02* | (2006.01) |
| *C09D 7/63* | (2018.01) |
| *C09D 7/45* | (2018.01) |
| *A61K 8/33* | (2006.01) |
| *A61K 8/41* | (2006.01) |
| *A61K 8/44* | (2006.01) |
| *A61K 8/49* | (2006.01) |
| *A61K 8/73* | (2006.01) |
| *A61K 8/85* | (2006.01) |
| *A61Q 3/02* | (2006.01) |
| *C08K 5/109* | (2006.01) |
| *C08K 5/17* | (2006.01) |

(52) U.S. Cl.
CPC ............. *C09D 4/06* (2013.01); *A61K 8/33* (2013.01); *A61K 8/416* (2013.01); *A61K 8/44* (2013.01); *A61K 8/494* (2013.01); *A61K 8/4986* (2013.01); *A61K 8/731* (2013.01); *A61K 8/85* (2013.01); *A61Q 3/02* (2013.01); *C08G 63/21* (2013.01); *C08J 3/24* (2013.01); *C09D 7/20* (2018.01); *C09D 7/45* (2018.01); *C09D 7/63* (2018.01); *C09D 167/02* (2013.01); *A61K 2800/95* (2013.01); *C08J 2367/02* (2013.01); *C08K 5/109* (2013.01); *C08K 5/17* (2013.01)

(58) Field of Classification Search
CPC ... C09D 4/06; C09D 7/20; C09D 7/45; C09D 7/63; C08K 5/109; C08K 5/17
See application file for complete search history.

(56) References Cited

U.S. PATENT DOCUMENTS

| | | | |
|---|---|---|---|
| 3,981,984 A | 9/1976 | Signorino | |
| 4,602,061 A * | 7/1986 | Akkerman | ............ C08F 283/00 525/10 |
| 5,945,489 A * | 8/1999 | Moy | ...................... C08G 16/00 522/135 |
| 8,003,169 B2 | 8/2011 | Misev et al. | |
| 8,962,725 B2 | 2/2015 | Brinkhuis et al. | |
| 9,181,452 B2 | 11/2015 | Brinkhuis et al. | |

(Continued)

FOREIGN PATENT DOCUMENTS

| | | | |
|---|---|---|---|
| EP | 2457846 | * | 5/2012 |
| WO | 2011121085 A1 | | 10/2011 |

(Continued)

OTHER PUBLICATIONS

International Search Report and Written Opinion for PCT Application No. PCT/US18/37241; dated Aug. 28, 2018; 16 pages.
(Ochemonline) PKa data; webpage, URL=http://www.ochemonline.com/PKa_data; Sep. 23, 2010; 2 pages.
U.S. Appl. No. 15/621,504, filed Jun. 13, 2017
U.S. Appl. No. 16/007,239, filed Jun. 13, 2018.
U.S. Appl. No. 16/007,177, filed Jun. 13, 2018.
International Patent Application No. PCT/US2017/037176 filed Jun. 13, 2017.
International Patent Application No. PCT/US2018/037247 filed Jun. 13, 2018.

(Continued)

*Primary Examiner* — Yanzhi Zhang
(74) *Attorney, Agent, or Firm* — Morgan, Lewis & Bockius LLP

(57) ABSTRACT

A coating composition containing a crosslinkable coating composition. The coating system comprises: ingredient A that has at least two protons that can be activated to form a Michael carbanion donor; ingredient B that functions as a Michael acceptor having at least two ethylenically unsaturated functionalities each activated by an electron-withdrawing group; and a catalyst system. In one embodiment, the catalyst system comprises diethyl carbonate, quaternary ammonium hydroxide or quaternary ammonium alkoxide, ethanol and 4-6 wt. % water. In another embodiment, the catalyst system comprises carbon dioxide, quaternary ammonium hydroxide or quaternary ammonium alkoxide, ethanol and 2-4 wt. % water. In certain embodiments, the coating composition optionally further comprising ammonium carbamate ($H_2NR_8R_9+$—OC=$ONR_8R_9$), wherein $R_8R_9$ are each independently selected from hydrogen, a linear or branched substituted or unsubstituted alkyl group having 1 to 22 carbon atoms; 1 to 8 carbon atoms; 1 to 3 carbon atoms.

18 Claims, No Drawings

(56) References Cited

U.S. PATENT DOCUMENTS

| | | | |
|---|---|---|---|
| 9,181,453 B2 | 11/2015 | Brinkhuis et al. | |
| 9,260,626 B2 | 2/2016 | Brinkhuis et al. | |
| 9,284,423 B2 | 3/2016 | Brinkhuis et al. | |
| 9,238,187 B2 | 5/2016 | Mestach et al. | |
| 9,534,081 B2 | 1/2017 | Brinkhuis et al. | |
| 2004/0171721 A1 | 9/2004 | Esemplare | |
| 2009/0269595 A1* | 10/2009 | Chung | C09D 5/004 |
| | | | 428/457 |
| 2013/0041091 A1* | 2/2013 | Brinkhuis | C09D 167/02 |
| | | | 524/513 |
| 2013/0053505 A1* | 2/2013 | Brinkhuis | C08K 5/098 |
| | | | 524/539 |
| 2013/0072641 A1 | 3/2013 | Mestach et al. | |
| 2014/0220252 A1 | 8/2014 | Brinkhuis et al. | |
| 2014/0221542 A1 | 8/2014 | Brinkhuis et al. | |
| 2015/0376472 A1 | 12/2015 | Bzowej et al. | |
| 2016/0060389 A1 | 3/2016 | Brinkhuis et al. | |
| 2016/0060482 A1 | 3/2016 | Brinkhuis et al. | |
| 2016/0115344 A1 | 4/2016 | Brinkhuis et al. | |
| 2016/0168320 A1 | 6/2016 | Brinkhuis et al. | |
| 2016/0311957 A1 | 10/2016 | Mestach et al. | |
| 2016/0333199 A1 | 11/2016 | Akkerman et al. | |
| 2018/0000720 A1 | 1/2018 | Ijdo et al. | |

FOREIGN PATENT DOCUMENTS

| | | | |
|---|---|---|---|
| WO | 2011124663 A1 | | 10/2011 |
| WO | 2011124664 A1 | | 10/2011 |
| WO | 2011124665 A1 | | 10/2011 |
| WO | 2013050624 | * | 2/2013 |
| WO | 2013050574 A1 | | 4/2013 |
| WO | 2013050623 A1 | | 4/2013 |
| WO | 2016166334 A1 | | 10/2016 |
| WO | 2016166361 A1 | | 10/2016 |
| WO | 2016166365 A1 | | 10/2016 |
| WO | 2016166369 A1 | | 10/2016 |
| WO | 2016166371 A1 | | 10/2016 |
| WO | 2016166381 A1 | | 10/2016 |

OTHER PUBLICATIONS

International Patent Application No. PCT/US2018/037239 filed Jun. 13, 2018.

International Search Report for International Patent Application No. PCT/US18/37239, dated Jun. 13, 2018.

International Search Report issued for application, PCT/US17/37176, dated Aug. 29, 2017.

Written Opinion issued for application, PCT/US17/37176, dated Aug. 29, 2017.

John, "Novel Switchable Systems and Applications", A Thesis Presented to the Academic Faculty, Georgia Institute of Technology (2007).

Khunsupat, "Polly(Allylamine) and Derivatives for CO2 Capture from Flue Gas or Ultra-Dilute Gas Streams Such as Ambient Air", A Thesis Presented to the Academic Faculty, Georgia Institute of Technology (2007).

Wildgoode et al., "Electrolosis of Ammonium Carbamate: A Voltammetric and X-Ray Photoelectron Spevtroscopic Investigation into the Modification of Carbon Electrodes", Int. J. Electrochem. Sci., vol. 2, pp. 809-819 (2007).

Office Action issued in U.S. Appl. No. 15/621,504 dated Dec. 17, 2018; 10 pages.

Office Action issued in U.S. Appl. No. 15/621,504 dated Jul. 12, 2019; 10 pages.

Office Action issued in U.S. Appl. No. 15/621,504 dated Nov. 8, 2019; 11 pages.

* cited by examiner

COATING SYSTEM

CROSS-REFERENCE TO RELATED APPLICATIONS

This application claims priority benefit from U.S. Provisional Patent Application 62/518,791 filed Jun. 13, 2017 which is incorporated by reference herein in its entirety.

FIELD OF THE INVENTION

The invention provides for a coating composition containing a carbonate catalyst system with water.

BACKGROUND

The coatings industry continues to develop new chemistries as performance requirements for decorative and functional coatings evolve. Drivers for change are varied and these can include: regulatory controls to reduce VOC emissions, concerns about toxic hazards of coating raw materials, a desire for cost reduction, commitments to sustainability, and a need for increased product effectiveness.

Highly crosslinked, durable coating compositions can be achieved using Michael addition chemistry. The Michael addition reaction involves the nucleophilic addition of a Michael donor, such as a carbanion or another nucleophile to a Michael acceptor, such as an α,β-unsaturated carbonyl. As such, the base catalyzed addition of activated methylene moieties to electron deficient C=C double bonds are known in coatings applications. Representative examples of suitable materials that can provide activated methylene or methine groups are generally disclosed in U.S. Pat. No. 4,871,822, which resins contain a methylene and/or monosubstituted methylene group in the alpha-position to two activating groups such as, for example, carbonyl, cyano, sulfoxide and/or nitro groups. Preferred are resins containing a methylene group in the alpha-position to two carbonyl groups, such as malonate and/or acetoacetate group-containing materials, malonates being most preferred. The α,β-unsaturated carbonyl typically is an acrylate material and representative materials have been disclosed in U.S. Pat. No. 4,602,061. The Michael reaction is fast, can be carried out at ambient temperatures and gives a chemically stable crosslinking bond without forming any reaction by-product.

A typical crosslinkable coating composition comprises a resin ingredient A (Michael donor), a resin ingredient B (Michael acceptor) and a base to start and catalyze the Michael addition reaction. The base catalyst should be strong enough to abstract, i.e. activate a proton from resin ingredient A to form the Michael donor carbanion species. Since the Michael addition cure chemistry can be very fast, the coating formulator is challenged to control the speed of the reaction to achieve an acceptable balance of pot life, open time, tack free time and cure time. Pot life is defined as the amount of time during which the viscosity of a mixed reactive system doubles. Working life or working time informs the user how much time they have to work with a reactive two part system before it reaches such a high state of viscosity, or other condition, that it cannot be properly worked with to produce an acceptable application result. Gel time is the amount of time it takes for a mixed, reactive resin system to gel or become so highly viscous that it has lost fluidity. The open time of a coating is a practical measure of how much time it takes for a drying or curing coating to reach a stage where it can no longer be touched by brush or roller when applying additional coating material without leaving an indication that the drying or curing coating and newly applied coating did not quite flow together. These indications normally take the form of brush or roller marks and sometimes a noticeable difference in sheen levels. The tack free time is the amount of time it takes for a curing or drying coating to be no longer sticky to the touch, i.e. the time for a system to become hard to the touch, with no tackiness. Cure time is the amount of time it takes for a coating system to reach full final properties.

The Michael reaction starts the very moment when coating resin ingredients A and B are mixed together with a suitable base. Since it is a fast reaction, the material in a mixing pot starts to crosslink and the fluid viscosity starts to rise. This limits the pot life, working time and general use as a coating. A dormant initiator that is essentially passive while coating material remains in a mixing vessel but that activates the Michael addition reaction upon film formation allows for longer pot life and working time, yet would show good open time, tack free time and cure time. Hence, the application of dormant initiator technology can provide the formulator with tools to control the speed of the reaction in order to achieve desirable cure characteristics.

U.S. Pat. No. 8,962,725 describes a blocked base catalyst for Michael addition, which is based on substituted carbonate salts. Preferred Michael donor resins are based on malonate and Michael acceptor resins are acrylates. The substituted carbonates can bear substituents, but these should not substantially interfere with the crosslinking reaction between malonate and acrylate. The carbonate salts release carbon dioxide and a strong base upon activation by means of film formation. The base is either hydroxide or alkoxide. Before practical pot life and gel times are achieved with acceptable curing characteristics, the carbonate requires presence of a certain amount of water in the coating formulation for the blocking of the base to become effective. All disclosed blocked carbonate examples utilize methanol and/or water.

SUMMARY OF INVENTION

In one embodiment, the present invention provides for a coating composition containing a crosslinkable coating composition comprising: ingredient A that has at least two protons that can be activated to form a Michael carbanion donor; ingredient B that functions as a Michael acceptor having at least two ethylenically unsaturated functionalities each activated by an electron-withdrawing group; and a catalyst system. In one embodiment, the catalyst system comprises diethyl carbonate, quaternary ammonium hydroxide or quaternary ammonium alkoxide, ethanol and 4-6 wt. % water. In another embodiment, the catalyst system comprises carbon dioxide, quaternary ammonium hydroxide or quaternary ammonium alkoxide, ethanol and 2-4 wt. % water. In certain embodiments, the coating composition optionally further comprising ammonium carbamate ($H_2NR_8R_9+$—$OC=ONR_8R_9$), wherein $R_8R_9$ are each independently selected from hydrogen, a linear or branched substituted or unsubstituted alkyl group having 1 to 22 carbon atoms; 1 to 8 carbon atoms; 1 to 3 carbon atoms.

In one embodiment, the present invention provides a coating composition wherein ingredient A is selected from the group consisting of compounds, oligomers or polymers. In one such embodiment, ingredient A is independently selected from a malonate group containing compound, a malonate group containing oligomer, a malonate group containing polymer, an acetoacetate group containing compound, an acetoacetate group containing oligomer, an acetoacetate group containing polymer or combinations thereof. In another such embodiment, the malonate group containing compound, malonate group containing oligomer, malonate group containing polymer, an acetoacetate group containing compound, acetoacetate group containing oligomer, or acetoacetate group containing polymer are each selected from the group consisting of: polyurethanes, polyesters, polyacrylates, epoxy polymers, polyamides, polyesteramides or polyvinyl polymers, wherein such compounds, oligomers or polymers have a malonate group or acetoacetate group located in a main chain of such compound or oligomer or polymer or a side chain of such compound or oligomer or polymer.

In one embodiment, the present invention provides a coating composition wherein wherein ingredient B is selected from the group consisting of acrylates, fumarates, maleates and combinations thereof. In one such embodiment, the acrylate is independently selected from the group consisting of hexanediol diacrylate, trimethylol propane triacrylate, pentaerythritol triacrylate, di-trimethylolpropane tetraacrylate bis(2-hydroxyethyl acrylate), trimethylhexyl dicarbamate, bis(2-hydroxyethyl acrylate) 1,3,3-trimethylcyclohexyl dicarbamate, bis(2-hydroxyethyl acrylate) methylene dicyclohexyl dicarbamate and combinations thereof.

In one embodiment, the present invention provides a coating composition wherein ingredient B is independently selected from the group consisting of polyesters, polyurethanes, polyethers and/or alkyd resins each containing at least two pendant ethylenically unsaturated groups each activated by an electron-withdrawing group.

DETAILED DESCRIPTION

The invention disclosed here is a crosslinkable composition comprising a resin ingredient A (Michael donor), a resin ingredient B (Michael acceptor) and a catalyst system C. The invention generally is useful as a coating composition.

Resin ingredient A (Michael donor): Resin ingredients A are compounds, oligomers or polymers that contain functional groups that have reactive protons that can be activated to produce a carbanion Michael donor. In one embodiment, the functional group can be a methylene or methine group and resins have been described in U.S. Pat. Nos. 4,602,061 and 8,962,725 for example. In one embodiment, resin ingredients A are those derived from malonic acid or malonate esters, i.e. malonate. Oligomeric or polymeric malonate compounds include polyurethanes, polyesters, polyacrylates, epoxy resins, polyamides, polyesteramides or polyvinyl resins each containing malonate groups, either in the main chain or the side chain or in both.

In one embodiment, polyurethanes having malonate groups may be obtained, for instance, by bringing a polyisocyanate into reaction with a hydroxyl group containing ester or polyester of a polyol and malonic acid/malonates, by esterification or transesterification of a hydroxyfunctional polyurethane with malonic acid and/or a dialkyl malonate. Examples of polyisocyanates include hexamethylenediisocyanate, trimethylhexamethylene diisocyanate, isophorone diisocyanate, toluene diisocyanate and addition products of a polyol with a diisocyanate, such as that of trimethylolpropane to hexamethylene diisocyanate. In one embodiment, the polyisocyanate is selected from isophorone diisocyanate and trimethyhexamethylene diisocyanate. In another embodiment, the polyisocyanate is isophorone diisocyanate. In some embodiments, hydroxyfunctional polyurethanes include the addition products of a polyisocyanate, such as the foregoing polyisocyanates, with di- or polyvalent hydroxy compounds, including diethyleneglycol, neopentyl glycol, dimethylol cyclohexane, trimethylolpropane, 1,3-propandiol, 1,4-butanediol, 1,6-hexanediol and polyether polyols, polyester polyols or polyacrylate polyols. In some embodiments, the di- or polyvalent hydroxy compounds include diethyleneglycol, 1,3-propanediol, 1,4-butanediol and 1,6-hexanediol. In other embodiments, the di- or polyvalent hydroxy compounds include diethyleneglycol and 1,6-hexanediol.

In one embodiment, malonic polyesters may be obtained, for instance, by polycondensation of malonic acid, an alkylmalonic acid, such as ethylmalonic acid, a mono- or dialkyl ester of such a carboxylic acid, or the reaction product of a malonic ester and an alkylacrylate or methacrylate, optionally mixed with other di- or polycarboxylic with one or more dihydroxy and/or polyhydroxy compounds, in combination or not with mono hydroxy compounds and/or carboxyl compounds. In some embodiments, polyhydroxy compounds include compounds containing 2-6 hydroxyl group and 2-20 carbon atoms, such as ethylene glycol, diethyleneglycol, propylene glycol, trimethylol ethane, trimethylolpropane, glycerol, pentaerythritol, 1,4-butanediol, 1,6-hexanediol, cyclohexanedimethanol, 1,12-dodecanediol and sorbitol. In some embodiments, the polyhydroxyl compounds include diethylene glycol, propylene glycol, 1,4-butanediol and 1,6-hexanediol. In other embodiments, the polyhydroxyl compounds include propylene glycol and 1,6-hexanediol. In certain embodiments, the polyhydroxy may be a primary alcohol and in certain other embodiments, the polyhydroxy may be a secondary alcohol. Examples of polyols with secondary alcohol groups are 2,3-butanediol, 2,4-pentanediol and 2,5-hexanediol and the like.

In one embodiment, malonate group-containing polymers also may be prepared by transesterification of an excess of dialkyl malonate with a hydroxy functional polymer, such as a vinyl alcohol-styrene copolymer. In this way, polymers with malonate groups in the side chains are formed. After the reaction, the excess of dialkyl malonate may optionally be removed under reduced pressure or be used as reactive solvent.

In one embodiment, malonate group or acetoacetate group containing polymers may also be obtained from reaction with malonate or acetoacetonate with polyols, such as those polyols that are commercially sold for reaction with isocyanates to form polyurethane coatings.

In one embodiment, malonic epoxy esters may be prepared by esterifying an epoxy polymer with malonic acid or a malonic monoester, or by transesterifying with a dialkylmalonate, optionally in the presence of one or more other carboxylic acids or derivatives thereof.

In one embodiment, polyamides having malonate groups may be obtained in the same manner as polyesters, at least part of the hydroxy compound(s) being replaced with a mono- or polyvalent primary and/or secondary amine, such as cyclohexylamine, ethylene diamine, isophorone diamine, hexamethylene diamine, or diethylene triamine.

In some embodiments, such polyamide compounds can be obtained when 12-hydroxystearic acid is reacted with a diamine such as ethylenediamine. Such polyamides have secondary alcohol groups, which can be esterified with malonic acid or malonate in a second reaction step. In some embodiments, other diamines may also be used in the reaction with 12-hydroxystearic acid, for example: xylylenediamine, butylenediamine, hexamethylenediamine, dodecamethylenediamine, and even dimer amine, which is derived from dimer acid. Polyamines may also be used, but in a right stoichiometric ratio as to avoid gelling of the polyamide in the reactor. Lesquerolic acid may also be used in reactions with polyamines to yield polyamides bearing secondary alcohol groups, which can be used in reactions with malonate to form malonate containing compounds. Reactions that yield malonamides are much less desirable.

In some embodiments, the above mentioned malonate resins may be blended together to achieve optimized coatings properties. Such blends can be mixtures of malonate modified polyurethanes, polyesters, polyacrylates, epoxy resins, polyamides, polyesteramides and the like, but mixtures can also be prepared by blending various malonate modified polyesters together. In some other embodiments, various malonate modified polyurethanes can be mixed together, or various malonate modified polyacrylates, or malonate modified epoxy resins, or various malonate modified polyamides, malonate modified polyesteramides.

In certain embodiments, malonate resins are malonate group containing oligomeric esters, polyesters, polyurethanes, or epoxy esters having 1-100, or 2-20 malonate groups per molecule. In some such embodiments, the malonate resins should have a number average molecular weight in the range of from 250 to 10,000 and an acid number not higher than 5, or not higher than 2. Use may optionally be made of malonate compounds in which the malonic acid structural unit is cyclized by formaldehyde, acetaldehyde, acetone or cyclohexanone. In some embodiments, molecular weight control may be achieved by the use of end capping agents, typically monofunctional alcohol, monocarboxylic acid or esters. In one embodiment, malonate compounds may be end capped with one or more of 1-hexanol, 1-octanol, 1-dodecanol, hexanoic acid or its ester, octanoic acid or its esters, dodecanoic acid or its esters, diethyleneglycol monoethyl ether, trimethylhexanol, and t-butyl acetoacetate, ethyl acetoacetate. In one such embodiment, the malonate is end capped with 1-octanol, diethyleneglycol monoethyl ether, trimethylhexanol, t-butyl acetoacetate and ethyl acetoacetate. In another such embodiment, the malonate is end capped t-butyl acetoacetate, ethyl acetoacetate and combinations thereof.

Monomeric malonates may optionally be used as reactive diluents, but certain performance requirements may necessitate removal of monomeric malonates from resin ingredient A.

In some embodiments, resin ingredients A include oligomeric and/or polymeric acetoacetate group-containing resins. In some embodiments, such acetoacetate group-containing resins are acetoacetic esters as disclosed in U.S. Pat. No. 2,759,913, diacetoacetate resins as disclosed in U.S. Pat. No. 4,217,396 and acetoacetate group-containing oligomeric and polymeric resins as disclosed in U.S. Pat. No. 4,408,018. In some embodiments, acetoacetate group-containing oligomeric and polymeric resins can be obtained, for example, from polyalcohols and/or hydroxy-functional polyether, polyester, polyacrylate, vinyl and epoxy oligomers and polymers by reaction with diketene or transesterication with an alkyl acetoacetate. Such resins may also be obtained by copolymerization of an acetoacetate functional (meth)acrylic monomer with other vinyl- and/or acrylic-functional monomers. In certain other embodiments, the acetoacetate group-containing resins for use with the present invention are the acetoacetate group-containing oligomers and polymers containing at least 1, or 2-10, acetoacetate groups. In some such embodiments, such acetoacetate group containing resins should have Mn in the range of from about 100 to about 5000 g/mol, and an acid number of about 2 or less. Resins containing both malonate and acetoacetate groups in the same molecule may also be used.

In another embodiment, the above mentioned malonate group containing resins and acetoacetate group-containing resins may also be blended to optimize coatings properties as desired, often determined by the intended end application.

Structural changes at the acidic site of malonate or acetoacetate can alter the acidity of these materials and derivatives thereof. For instance, pKa measurements in DMSO show that diethyl methylmalonate (MeCH($CO_2$Et)$_2$) has a pKa of 18.7 and diethyl ethylmalonate (EtCH($CO_2$Et)$_2$) has a pKa of 19.1 whereas diethyl malonate ($CH_2$($CO_2$Et)$_2$) has a pKa of 16.4. Resin ingredient A may contain such substituted moieties and therewith show changes in gel time, open time, cure time and the like. For example, resin ingredient A may be a polyester derived from a polyol, diethyl malonate and diethyl ethylmalonate.

Resin ingredient B (Michael acceptor): Resin ingredients B (Michael acceptor) generally can be materials with ethylenically unsaturated moieties in which the carbon-carbon double bond is activated by an electron-withdrawing group, e.g. a carbonyl group in the alpha-position. In some embodiments, resin ingredients B are described in: U.S. Pat. Nos. 2,759,913, 4,871,822, 4,602,061, 4,408,018, 4,217,396 and 8,962,725. In certain embodiments, resin ingredients B include acrylates, fumarates and maleates.

In some embodiments, resin ingredients B are the acrylic esters of chemicals containing 2-6 hydroxyl groups and 2-20 carbon atoms. These esters may optionally contain hydroxyl groups. In some such embodiments, examples of such acrylic esters include hexanediol diacrylate, trimethylolpropane triacrylate, pentaerythritol triacrylate, di-trimethylolpropane tetraacrylate. In one such embodiment, acrylic esters include trimethylolpropane triacrylate, di-trimethylolproane tetraacrylate, dipentaerythritol hexaacrylate, pentaerythritol ethoxylated (EO)$_n$ tetraacrylate, trimethylolpropane ethoxylated(EO)$_n$ triacrylate and combinations thereof. In another embodiment, acrylamides may be used as a resin ingredient B.

In other embodiments, resin ingredients B are polyesters based upon maleic, fumaric and/or itaconic acid (and maleic and itaconic anhydride), and chemicals with di- or polyvalent hydroxyl groups, optionally including materials with a monovalent hydroxyl and/or carboxyl functionality.

In other embodiments, resin ingredients B are resins such as polyesters, polyurethanes, polyethers and/or alkyd resins each containing at least two pendant ethylenically unsaturated groups each activated by an electron-withdrawing group. These include, for example, urethane acrylates obtained by reaction of a polyisocyanate with an hydroxyl group-containing acrylic ester, e.g., an hydroxyalkyl ester of acrylic acid or a resins prepared by esterification of a polyhydroxyl material with acrylic acid; polyether acrylates obtained by esterification of an hydroxyl group-containing polyether with acrylic acid; polyfunctional acrylates obtained by reaction of an hydroxyalkyl acrylate with a polycarboxylic acid and/or a polyamino resin; polyacrylates obtained by reaction of acrylic acid with an epoxy resin; and polyalkylmaleates obtained by reaction of a monoalkylmaleate ester with an epoxy polymer and/or an hydroxy functional oligomer or polymer. In certain embodiments, polyurethane acrylate resins may be prepared by reaction of hydroxyalkyl acrylate with polyisocyanate. Such polyurethane acrylate resins independently include bis(2-hydroxyethyl acrylate) trimethylhexyl dicarbamate [2-hydroxyethyl acrylate trimethylhexamethylene diisocyanate (TMDI) adduct], bis(2-hydroxyethyl acrylate) 1,3,3-trimethylcyclohexyl dicarbamate [2-hydroxyethyl acrylate 1,3,3-trimethylcyclohexyl diisocyanate/isophorone diisocyanate (IPDI)

adduct], bis(2-hydroxyethyl acrylate) hexyl dicarbamate [2-hydroxyethyl acrylate hexamethylene diisocyanate (HDI) adduct], bis(2-hydroxyethyl acrylate) methylene dicyclohexyl dicarbamate [2-hydroxyethyl acrylate methylene dicyclohexyl diisocyanate (HMDI) adduct], bis(2-hydroxylethyl acrylate) methylenediphenyl dicarbamate [2-hydroxyethyl acrylate methylenediphenyl diisocyanate (MDI) adduct], bis(4-hydroxybutyl acrylate) 1,3,3-trimethylcyclohexyl dicarbamate [4-hydroxybutyl acrylate IPDI adduct], bis(4-hydroxybutyl acrylate) trimethylhexyl dicarbamate [4-hydroxybutyl acrylate TMDI adduct], bis(4-hydroxybutyl acrylate) hexyl dicarbamate [4-hydroxybutyl acrylate HDI adduct], bis(4-hydroxybutyl acrylate) methylene dicyclohexyl dicarbamate [4-hydroxybutyl acrylate HMDI adduct], bis(4-hydroxybutyl acrylate) methylenediphenyl dicarbamate [4-hydroxybutyl acrylate MDI adduct].

In other embodiments, resin ingredients B have unsaturated acryloyl functional groups. In other certain embodiments, resin ingredient B is independently selected from the group consisting of polyesters, polyurethanes, polyethers and/or alkyd resins each containing at least one pendant acryloyl functional group.

In certain embodiments, the acid value of the activated unsaturated group-containing material (resin ingredient B) is sufficiently low to not substantially impair the Michael addition reaction, for example less than about 2, and further for example less than 1 mg KOH/g.

As exemplified by the previously incorporated references, these and other activated unsaturated group containing resins, and their methods of production, are generally known to those skilled in the art, and need no further explanation here. In certain embodiments, the number of reactive unsaturated group ranges from 2 to 20, the equivalent molecular weight (EQW: average molecular weight per reactive functional group) ranges from 100 to 2000, and the number average molecular weight Mn ranges from 100 to 5000.

In one embodiment, the reactive part of resin ingredients A and B can also be combined in one A-B type molecule. In this embodiment of the crosslinkable composition both the methylene and/or methine features as well as the $\alpha,\beta$-unsaturated carbonyl are present in the same molecule, be it a monomer, oligomer or polymer. Mixtures of such A-B type molecules with ingredient A and B are also useful.

Each of the foregoing embodiments of resin ingredient A and resin ingredient B may be combined with the various embodiments of a catalyst system ingredient C, described below, to arrive at the inventions described herein. In one embodiment, resin ingredient A is a polyester malonate composition and resin ingredient B is a polyester acrylate. In another embodiment, resin ingredient A is a polyurethane malonate composition and resin ingredient B is a polyester acrylate. In another embodiment, resin ingredient A is a polyurethane malonate composition and resin ingredient B is a polyester acrylate. In another embodiment, resin ingredient A is a polyurethane malonate composition and resin ingredient B is a polyurethane acrylate. In another embodiment, resin ingredient A is a polyester malonate having acetoacetate end groups and resin ingredient B is a polyester acrylate. In yet another embodiment, resin ingredient A is a polyester malonate having acetoacetate end groups and resin ingredient B is a polyurethane acrylate. In still yet another embodiment, resin ingredient A is a polyester malonate having acetoacetate end groups and resin ingredient B is a mixture of polyester acrylate and polyurethane acrylate.

In the foregoing embodiments, the number of reactive protons for resin ingredients A, and the number of $\alpha,\beta$-unsaturated carbonyl moieties on resin ingredient B can be utilized to express desirable ratios and ranges for resin ingredients A and B. Typically, the mole ratio of reactive protons of ingredient A that can be activated with subsequent carbanion formation relative to the activated unsaturated groups on ingredient B is in the range between 10/1 and 0.1/1, or between 4/1 and 0.25/1, or between 3.3/1 and 0.67/1. However, the optimal amount strongly depends also on the number of reactive groups present on ingredients A and/or B.

The amount of catalyst system used, expressed as mole ratio of protons that can be abstracted to form an activated Michael donor species (e.g. the methylene group of malonate can provide two protons for reactions, while a methine group can provide one proton to form an activated species) relative to catalyst, ranges from about 1000/1 to 1/1, or from 250/1 to 10/1, or from 125/1 to 20/1 but the optimal amount to be used depends also on the amount of solvent present, reactivity of various acidic protons present on resin ingredients A and/or B.

Catalyst System C:

In one embodiment, the catalyst system comprises diethyl carbonate, a quaternary ammonium hydroxide or a quaternary ammonium alkoxide, ethanol and 4-6 wt. % water relative to total weight of the crosslinkable composition.

In another embodiment, the catalyst system comprising carbon dioxide, a quaternary ammonium hydroxide or a quaternary ammonium alkoxide, ethanol and 2-4 wt. % water relative to total weight of the crosslinkable composition.

Examples of a quaternary ammonium cations, either as hydroxides or alkoxides, include dimethyldiethylammonium, dimethyldipropylammonium, triethylmethylammonium, tripropylmethylammonium, tributylmethylammonium, tripentylmethylammonium, trihexylmethylammonium tetraethylammonium, tetrapropylammonium, tetrabutylammonium, tetrapentylammonium, tetrahexylammonium, benzyltrimethylammonium, benzyltriethylammonium, benzyltripropylammonium, benzyltributylammonium, benzyltripentyammonium, and benzyltrihexylammonium. The alkoxide is a conjugate base of an alcohol and examples of the alkoxide include ethoxide, isopropoxide and tert-butoxide.

In some embodiments, the catalyst system further comprises ammonium carbamate ($H_2NR_8R_9+$—$OC$=$ONR_8R_9$), wherein $R_8R_9$ are each independently selected from hydrogen, a linear or branched substituted or unsubstituted alkyl group having 1 to 22 carbon atoms; 1 to 8 carbon atoms; 1 to 3 carbon atoms.

In some embodiments, the ammonium carbamate is independently selected from ammonium carbamate, methylammonium methylcarbamate, ethylammonium ethylcarbamate, propylammonium propylcarbamate, isopropylammonium isopropylcarbamate, butylammonium butylcarbamate, isobutylammonium isobutylcarbamate, pentylammonium pentylcarbamate, and hexylammonium hexylcarbamate. In other embodiments, the ammonium carbamate is derived from carbamates independently selected from dimethyl ammonium dimethylcarbamate, diethylammonium diethylcarbamate, dipropylammonium dipropylcarbamate, dibutylammonium dibutylcarbamate, diisobutylammonium diisobutylcarbamate, dipentylammonium dipentylcarbamate, dihexylammonium dihexylcarbamate, and dibenzylammonium dibenzylcarbamate. In other embodiments, the ammonium carbamate is derived from carbamates independently selected from N-methylethylammonium methylethylcarbamate, N-methylpropylammonium methylpropylcarbamate, and N-methylbenzylammonium methylbenzylcarbamate. In some certain embodiments, the ammonium carbamate is derived from carbamates independently selected from dimethylammonium dimethylcarbamate, diethylammonium diethylcarbamate, dipropylammonium dipropylcarbamate, N-methylethylammonium methylethylcarbamate, and N-methylpropylammonium methylpropylcarbamate.

The crosslinkable composition of this invention preferably contains some solvent. The coating formulator may choose to use an alcohol, or a combination of alcohols as solvent for a variety of reasons. Other solvents like ethylacetate or butylacetate may also be used, potentially in combination with alcohol solvents. Ethanol is a preferred solvent. Isopropyl alcohol also is a potential solvent. Methanol is not preferred as a solvent because of health and safety risks. Other oxygenated, polar solvents such as ester or ketones for instance, are also suitable and can be used, potentially in combination with alcohol. Other organic solvents may also be used.

The crosslinkable composition of this invention may also be formulated without solvent in some cases. In other embodiments, the crosslinkable coating contains typically at least 5 wt. % of solvent, preferably between 5 wt. % and 45 wt. %, more preferable between 5 wt. % and 35 wt. %, but preferable not more than 60 wt. % because of VOC restrictions. In such embodiments, the organic solvent is independently selected from the group consisting of an alcohol, ester, ether, glycol ether, ketone, aromatic and combinations thereof. In certain embodiments the alcohol is independently selected from the group consisting of ethanol, iso-propanol, butanol, iso-butanol, t-butanol and combinations thereof.

The crosslinkable composition useful as a coating can be formulated as a one component, a two component system or a three component system. In an embodiment of a two component system, catalyst system C is added to a mixture of ingredients A and B just prior to use; ingredient D may optionally be added to the catalyst system C or the mixture of ingredients A and B. In an alternative embodiment, ingredients A and C are mixed, and ingredient B is added prior to use ingredient; D may optionally be added to the mixture of ingredient A and catalyst system C or ingredient B. In yet another embodiment, ingredient A is added to a mixture of ingredients B and catalyst system C prior to use; ingredient D may optionally be added to ingredient A or the mixture of ingredient B and catalyst system C. In certain embodiments, pot life, working time and gel time can be adjusted by selection of the catalyst system, the amount used in the crosslinkable composition, presence of additional ammonium carbamate and to a certain extent the amount of solvent and/or water. A gel time of hours, and even days can be readily achieved, and gel times of weeks are possible. As such, the catalyst system allows for an opportunity to formulate a three component paint system. In such embodiment of a one component system, ingredients A, B, C and D are mixed together, optionally with other ingredients to formulate a paint, which is then canned and stored until use. In certain embodiments, a one component system can be enhanced by means of using excess carbon dioxide gas over the crosslinkable composition as to further improve pot life and gel time. For instance, a paint composition formulated according to the invention may have a protective atmosphere of carbon dioxide over the paint volume; and in yet another embodiment, a container containing the crosslinkable composition may even be pressurized with carbon dioxide. In another embodiment, a one component system containing ingredients A, B and C are in a container filled to capacity with essentially no space remaining for other solids, liquid or gaseous ingredients and optionally containing ammonium carbamate. In yet another embodiment, additional ammonium carbamate may further enhance stability in such one component coating formulations.

In another embodiment, the present invention provides for the crosslinkable coating composition wherein ingredient A, ingredient B and the catalyst system are contained in a container having two or more chambers, which are separated from one another. In one such embodiment, ingredient A and ingredient B are contained in separate chambers to inhibit any reaction. In another such embodiment, the catalyst system is contained in the chamber having ingredient A, and optionally containing $CO_2$ and/or ammonium carbamate. In another such embodiment, the catalyst system is contained in the chamber having ingredient B, and optionally containing $CO_2$ and/or ammonium carbamate.

In another embodiment, the present invention provides for the crosslinkable coating composition such that ingredient A and ingredient B are contained in the same chamber and the catalyst system is contained in a separate chamber to inhibit any reaction and said separate chamber optionally containing $CO_2$ and/or ammonium carbamate.

The number of reactive protons for ingredients A, and the number of $\alpha,\beta$-unsaturated carbonyl moieties on resin ingredient B can be utilized to express desirable ratio's and ranges for ingredients A and B. Typically, the mole ratio of reactive protons of ingredient A that can be activated with subsequent carbanion formation relative to the activated unsaturated groups on ingredient B is in the range between 10/1 and 0.1/1, preferably between 4/1 and 0.25/1, and more preferably 3.3/1 and 0.67/1. However, the optimal amount strongly depends also on the number of such active functionalities present on ingredients A and/or B. Although good tack free time may be obtained over a wide ratio range, coatings properties, such as hardness for instance may show a smaller preference range.

The crosslinkable composition of this invention comprising ingredients A, B and C may optionally contain an additional ingredient D, which once activated, can react with the Michael acceptor. Ingredient D has one or more reactive protons that are more reactive, i.e. more acidic than those of ingredient A (the pKa of ingredient D is lower than that of ingredient A). The reactive protons of ingredient D are present at a fraction based on the reactive protons of ingredient A. The fraction ranges from 0 to 0.5, more preferably from 0 to 0.35, even more preferable between 0 and 0.15.

Examples of ingredient D include; succinimide, isatine, ethosuximide, phthalimide, 4-nitro-2-methylimidazole, 5,5-dimethylhydantioin, phenol, 1,2,4-triazole, ethylacetoacetate, 1,2,3-triazole, ethyl cyanoacetate, benzotriazole, acetylacetone, benzenesulfonamide, 1,3-cyclohexanedione, nitromethane, nitroethane, 2-nitropropane, diethylmalonate, 1,2,3-triazole-4,5-dicarboxylic acid ethyl ester, 1,2,4-triazole-3-carboxylic acid ethyl ester, 3-Amino-1,2,4-triazole, 1H-1,2,3-triazole-5-carboxylic acid ethyl ester, 1H-[1,2,3]triazole-4-carbaldehyde, morpholine, purines such as purine, adenine, guanine, hypoxanthine, xanthine, theobromine, caffeine, uric acid and isoguanine; pyrimidines, such as thymine and cytosine; uracil, glycine, ethanimidamide, cysteamine, allantoin, N,N-dimethylglycine, allopurinol, N-methylpyrrolidine, benzeneboronic acid, salicyl aldehyde, 3-hydroxyb enzaldehyde , 1-naphthol, methylphenidate and Vitamin E.

In another embodiments, ingredient D may be incorporated into resin ingredient A. In such embodiments, substituted succinimides, including hydroxyl group containing succinimide derivatives, 3-hydroxy-2,5-pyrrolidinedione and 3-(hydroxymethyl)-2,5-pyrrolidinedione, or carboxylic acid group containing succinimide derivative, 2,5-dioxo-3-pyrrolidinecarboxylic acid can undergo condensation reactions with either acid/ester groups or hydroxyl groups at the end of resin A polymer chain, where the succinimide moiety will be incorporated into the polymer backbone as end cap.

The amount of catalyst system used, expressed as mole ratio of protons that can be abstracted to form an activated Michael donor species (e.g. the methylene group of malonate can provide two protons for reactions, while a methine group can provide one proton to form an activated species) relative to catalyst system, ranges from about 1000/1 to 1/1, more preferably from 250/1 to 10/1, even more preferable from 125/1 to 20/1 but the optimal amount to be used depends also on the amount of solvent present, reactivity of various acidic protons present on ingredient A and, if present, ingredient D, on pigments or dyes present in the system, on the number of active functionalities present on ingredients A and/or B and the like. Hence, the optimal amount needs to be determined experimentally to arrive at preferred curing characteristics.

Certain embodiments of the formulation may optionally comprise resins that may act as film formers, adhesion promoters, and aids to removal. These resins may also qualify as solvent-dissolvable resins.

The cross-linkable coating composition of this invention can comprise additives such as wetting agents, defoamers, rheological control agents, ultraviolet (UV) light stabilizers, dispersing agents, flow and leveling agents, optical brighteners, gloss additives, radical inhibitors, radical initiators, adhesions promotors, gloss additives, radical inhibitors, radical initiators, plasticizers and combinations thereof. The selection of these materials and additives will, of course, depend on the intended use of the coating composition. However, all these materials need to be carefully screened as some of these may react with the catalyst system and therefore are not suitable for use in the crosslinkable composition should such a reaction occur and significantly interfere with the curing process. The above described materials and additives are commonly used in the coatings industry and are well known to one skilled in the art and need not be further described here.

In certain embodiments, the crosslinkable composition of this invention, ingredient A, ingredient B and the catalyst system are contained in a container having two or more chambers, which are separated from one another. In one such embodiment, ingredient A and ingredient B are contained in separate chambers to inhibit any reaction. In another embodiment, the catalyst system is contained in the chamber having ingredient A, and optionally containing $CO_2$. In yet another embodiment, ingredient A and ingredient B are contained in the same chamber and the catalyst system is contained in a separate chamber to inhibit any reaction and said separate chamber optionally containing $CO_2$. In still yet another embodiment, ingredient A and ingredient B and catalyst system are contained in a container having a single chamber, wherein the container optionally (i) contains $CO_2$.

The following examples further describe and demonstrate illustrative embodiments within the scope of the present invention. The examples are given solely for illustration and are not to be construed as limitations of this invention as many variations are possible without departing from the spirit and scope thereof.

Coating Testing

Tack free time was evaluated by lightly pressing a gloved index finger periodically onto the coating. The time when visible marks in the film are no longer left by the pressed finger, was then recorded as the tack free time.

Gel time was taken as the amount of time it takes for a mixed, reactive resin system to gel or become so highly viscous that it has lost fluidity. Typically, the various ingredients were charged into a 4 ml vial and closed with headspace volume as constant as possible to allow for comparison and the sample was kept at room temperature and tilted at regular time intervals to determine whether the material still flows. If no flow is observed during tiling, the vial was held upside down and if no further flow occurs the materials is gelled.

EXAMPLE 1

General Synthesis of Catalyst System from Diethylcarbonate.

Most of the methanol solvent from a 40 g tetrabutylammonium hydroxide (TBA OH) solution in methanol (1 M) was removed with a rotary evaporator. The material was not allowed to become completely dry without solvent as dry quaternary ammonium hydroxide base is susceptible to decomposition. Next, 40 grams of ethanol was added and most of the solvent was again removed. This procedure was repeated at least two more times until the methanol effectively had been replaced as determined by NMR. The solution strength is determined by titration (typically 1.7 mmol base/g solution). Next, a precise amount of the TBA OH in solution was mixed with diethyl carbonate (DEtC) in a 1:5 molar ratio respectively and stirred for 1 hour at room temperature using magnetic stirrer. The final clear catalyst system was analyzed by means of titration and NMR. In a similar manner, clear solutions were obtained in 1-propanol and 2-propanol. A solution made using the TBA OH base in methanol resulted in white precipitate which is removed by centrifuge followed by filtration using 0.45µ syringe filter. Transesterification reaction products were observed in the NMR for all cases where the carbonate alkyl group was different from the solvent, e.g. ethanol formation was observed when DEtC was added to TBA OH in isopropanol and isopropyl groups associated with carbonates were also observed.

EXAMPLE 2

Malonate Resin (I) Synthesis.

A 500 ml reactor was charged with 149.8 g of Polyethylene glycol (PEG 300), 100 g of diethyl malonate (DEM), 32.5 g of 1-octanol and 4-5 drops of titanium (IV) butoxide. The reactor was equipped with a Dean-Stark apparatus, mechanical stirrer, nitrogen flow and heating equipment. The mixture was heated to about 180° C. with stirring under nitrogen atmosphere. During an eight hour reaction time, about 70 ml of ethanol was collected. The final product was a lightly yellow colored liquid with less than 0.15 wt. % of residual DEM as determined by gas chromatography (GC). Gel permeation chromatography (GPC) analysis showed Mw/Mn (PDI) of 4191/2818 (1.49) in gram/mole and a malonate methylene equivalent molecular weight of 360 g/mole.

EXAMPLE 3

Blocked Catalyst Effectiveness.

Diethylcarbonate (DEtC) derived catalysts were prepared in methanol, ethanol, 1-propanol and 2-propanol in Example 1. Varying amounts of water were added to the catalyst solutions. The catalyst solutions were then tested in formulations prepared from malonate resin (I) of Example 2 and trimethylolpropane triacrylate (TMPTA) using a molar ratio for malonate methylene $CH_2$ to TMPTA acrylate to catalyst of 3:2:0.2 respectively. All the materials of the formulation were mixed well prior to observing gel time and applying a 3 mil test film on a polycarbonate substrate to test curing behavior. Results are shown in Table 1. The amount of water and alcohol solvent is expressed as percentage of the final crosslinkable formulation. In the absence of water, the catalyst solutions as synthesized per Example 1 are not active as a blocked catalyst when the solvent is ethanol, 1-propanol or 2-propanol. No tack free time could be measured because the resin-carbonate catalyst mixture polymerized and cured immediately and an instant gel was formed. A significant amount of water is needed before the effect of a blocked catalyst can be observed. Only the methanol based catalyst shows desirable gel times measured in hours, which can be increased further when water is added to the formulation.

TABLE 1

| Solvent | % Water | % Solvent | Tack free time [sec] | Gel time |
|---|---|---|---|---|
| Methanol | 0.0 | 14.4 | <90 | 16 hrs |
|  | 3.3 | 14.0 | 110 | 9 days |
|  | 3.8 | 13.9 | 110 | 13 days |
|  | 4.2 | 13.8 | <120 | >13 days |
|  | 5.3 | 13.7 | <120 | >18 days |
| Ethanol | 0.0 | 14.4 | — | <30 sec |
|  | 3.3 | 14.0 | — | <30 sec |
|  | 3.8 | 13.9 | — | <30 sec |
|  | 4.2 | 13.8 | <180 | 2 hrs |
|  | 5.3 | 13.7 | <180 | >5 hrs |
| 1-Propanol | 0.0 | 14.4 | — | <30 sec |
|  | 3.3 | 14.0 | — | <30 sec |
|  | 3.8 | 13.9 | <180 | 40 sec |
|  | 4.2 | 13.8 | <180 | 2 min |
|  | 5.3 | 13.7 | <180 | 2.0 hrs |
| 2-Propanol | 0.0 | 14.4 | — | <30 sec |
|  | 3.3 | 14.0 | — | <30 sec |
|  | 3.8 | 13.9 | — | 1 min |
|  | 4.2 | 13.8 | — | <5 min |
|  | 5.3 | 13.7 | nm* | 20 min |

*not measured

EXAMPLE 4

General Synthesis of a Catalyst System by Reacting Base and Carbon Dioxide.

Tributylmethylammonium chloride (TBMA Cl), (10 g) was dissolved in anhydrous ethanol (8.7 g) and mixed with a 20 wt. % solution of potassium ethoxide in anhydrous ethanol (17.8 g) in 1:1 molar ratio. The mixture was allowed to mix under agitation for 30 min, and was then centrifuged at 5000 rpm for 15 min to remove potassium chloride precipitate. The concentration of the tributylmethylammonium quat ethoxide was determined potentiometrically by titrating it against 0.1 N HCl solution. Dry carbon dioxide gas was passed through the tributylmethylammonium quat ethoxide solution with stirring for 1 hour as to obtain the desired catalyst system. The tributylmethylammoniumethylcarbonate (TBMA EC) solution in ethanol is light yellow in color and is characterized by means of acid and base titrations (potentiometric and with indicator) and NMR.

A tributylmethylammonium isopropylcarbonate (TBMA IPC) catalyst solution was prepared in a similar manner. Tributylmethylammonium chloride was reacted with potassium tert-butoxide in isopropanol followed by centrifugation prior to passing carbon dioxide through the solution. NMR analysis confirmed isopropylcarbonate as the anionic species.

EXAMPLE 5

Malonate Resin (II) Synthesis

A 3 L reactor was charged with 700.0 g of diethyl malonate, 619.8 g of 1,6-hexanediol (HDO) and 227.5 g of ethyl acetoacetate (EAA). The reactor was equipped with a Dean-Stark apparatus, overhead mechanical stirrer, nitrogen flow and heating equipment. The mixture was heated to about 120° C. with stirring under nitrogen and then 0.62 g of phosphoric acid was added. Temperature was then increased to 145° C. and ethanol started to distill at this temperature. Temperature was then stepwise increased to 180° C. and continued until ethanol distillation stopped. In total, 588 ml of ethanol was collected. The reaction was then cooled to 120° C. and vacuum was applied for 4 hours while driving molecular weight. The final product is clear with less than 0.1% of residual monomer. GPC analysis showed Mw/Mn (PD) of 4143/1792 (2.31) in g/mole.

EXAMPLE 6

Basic Clear Coating Formulation

The TBMA EC solution of Example 4 was tested as a catalyst system. In a vial, 2.0 g of the malonate resin II of Example 5 was mixed with 2.68 g of DTMPTA, 0.4 g of BA and then 0.80 g of the TBMA EC solution was added. The complete formulation was mixed well prior to observing gel time and applying a 3 mil test film on a polycarbonate substrate to test coating curing behavior. A similar test was carried out with the TBMA IPC catalyst using 0.90 g of the TBMA IPC solution to keep molar amount of catalyst constant versus the resin. Data in Table 2 shows that a notably shorter gel time for the isopropanol based catalyst was observed.

TABLE 2

| Catalyst | Solvent | Tack free time [sec] | Gel time [min] |
|---|---|---|---|
| TBMA EC | Ethanol | 90 | 50 |
| TBMA IPC | 2-Propanol | 120 | 25 |

EXAMPLE 7

The procedure as per Example 6 was repeated except that varying amounts of dimethylammonium dimethylcarbamate (DMADMC) were added to the TBMA EC solution prior to adding said solution to the resin/DTMPTA solvent mix. The DMADMC was obtained from commercial sources and purity was checked via NMR. DMADMC is the reaction product between dimethylamine and carbon dioxide in a 2:1 molar ratio, albeit small deviations from this stoichiometry are possible in commercially available DMADMC materials. Such commercial materials may also contain ammonium carbonates depending on source purity. All ingredient amounts were kept the same and the DMADMC amount is thus on top of the formulation. Only in experiment #4, was DMADMC added to the resin/DTMPTA solvent mix rather than to the catalyst solution. The complete formulation was mixed well prior to observing gel time and applying a 3 mil test film on a polycarbonate substrate to test coating curing behavior. The ambient relative humidity was 48% while the temperature was 21° C. The absolute humidity was 8.8 [g/m3]. Results in Table 3 shows that addition of DMADMC greatly increases gel time while the tack free time only marginally increases unless significant amounts of DMADMC in excess to the catalyst are added. No significant effect of DMADMC addition on film properties were noted after cure.

TABLE 3

| # | DMADMC/carbonate catalyst (molar ratio) | Tack free time [m:s] | Gel time |
|---|---|---|---|
| 1 | 0 | 2:30 | 1 hr |
| 2 | 0.5 | 2:20 | 12 hr |
| 3 | 1 | 2:30 | 2 days |
| 4 | 1 | 2:45 | 2 days |
| 5 | 2 | 2:55 | 4 days |
| 6 | 5 | 4:00 | >4 days |

EXAMPLE 8

The procedure as per Experiment 6 was repeated using the TBMA EC catalyst solution of Example 4, except that varying amounts of water were added to either the resin/DTMPTA solvent mix (addition path I) or to the catalyst solution (addition path II). Once water was added and well mixed, then the catalyst solution was combined with the resin/DTMPTA solvent mix. The amount of water added was chosen so that the overall water content of the total formulation contained 0, 2, 4, 6, 8 or 10 wt. % water. The complete formulations were mixed well. Gel time was tested and the tack free time was determined after a 3 mil test film was applied on polycarbonate substrates.

TABLE 4

| # | Addition path | Wt. % Water | Tack free time [m:s] | Gel time |
|---|---|---|---|---|
| 1 | I | 0 | 2:40 | 1 hr 10 min |
| 2 | I | 2 | 3:05 | 5 hr |
| 3 | II | 2 | 3:30 | 4 hr |
| 4 | I | 4 | 3:50 | >9 hr, gelled O/N |
| 5 | II | 4 | 4:20 | >7 hrs, gelled O/N |
| 6 | I | 6 | 4:15 | >33 hrs, gelled O/N |
| 7 | II | 6 | 4:55 | >31 hrs, gelled O/N |
| 8 | I | 8 | 4:45 | >36 hrs, gelled O/N |
| 9 | I | 10 | 5:20 | 4 days |

List of Chemical Acronyms Used in the Examples
BA butylacetate
DEM diethyl malonate
DEtC diethyl carbonate
EAA ethyl acetoacetate
HDO 1,6-hexanediol
PEG 300 polyethylene glycol, Mw=300
TBA OH tetrabutylammonium hydroxide
TBMA Cl tributylmethylammonium chloride
TBMA EC tributylmethylammonium ethylcarbonate
TBMA IPC tributylmethylammonium isopropylcarbonate
TMPTA trimethylolpropane triacrylate The present disclosure may be embodied in other specific forms without departing from the spirit or essential attributes of the invention. Accordingly, reference should be made to the appended claims, rather than the foregoing specification, as indicating the scope of the disclosure. Although the foregoing description is directed to the preferred embodiments of the disclosure, it is noted that other variations and modification will be apparent to those skilled in the art, and may be made without departing from the spirit or scope of the disclosure.

What is claimed:

1. A coating composition containing a crosslinkable coating composition comprising:
   ingredient A that has at least two protons that can be activated to form a Michael carbanion donor;
   ingredient B that functions as a Michael acceptor having at least two ethylenically unsaturated functionalities each activated by an electron-withdrawing group;
   ammonium carbamate ($H_2NR_8R_9+$—$OC=ONR_8R_9$), wherein $R_8$, $R_9$ are each independently selected from hydrogen, a linear or branched substituted or unsubstituted alkyl group each having a number of carbon atoms selected from the group consisting of 1 to 22 carbon atoms; 1 to 8 carbon atoms; and 1 to 3 carbon atoms; and
   a catalyst system selected from the group consisting of
   (i) a catalyst system of diethyl carbonate, quaternary ammonium hydroxide or quaternary ammonium alkoxide, ethanol and optionally 4-6 wt.% water relative to total weight of the crosslinkable coating composition; and (ii) a catalyst system of carbon dioxide, quaternary ammonium hydroxide or quaternary ammonium alkoxide, ethanol and optionally 2-4 wt.% water relative to total weight of the crosslinkable coating composition.

2. The coating composition according to claim 1, wherein the ingredient A is independently selected from a malonate group containing compound, a malonate group containing oligomer, a malonate group containing polymer, an acetoacetate group containing compound, an acetoacetate group containing oligomer, an acetoacetate group containing polymer or combinations thereof.

3. The coating composition according to claim 2, wherein the malonate group containing compound, malonate group containing oligomer, malonate group containing polymer, an acetoacetate group containing compound, acetoacetate group containing oligomer, or acetoacetate group containing polymer are each selected from the group consisting of: polyurethanes, polyesters, polyacrylates, epoxy polymers, polyamides, polyesteramides or polyvinyl polymers, wherein such compounds, oligomers or polymers have a malonate group or acetoacetate group located in a main chain of such compound or oligomer or polymer or a side chain of such compound or oligomer or polymer.

4. The coating composition according to claim 3, wherein ingredient B is selected from the group consisting of acrylates, fumarates, maleates and combinations thereof.

5. The coating composition according to claim 4, wherein the acrylate is independently selected from the group consisting of hexanediol diacrylate, trimethylol propane triacrylate, pentaerythritol triacrylate, di-trimethylolpropane tetraacrylate, bis(2-hydroxyethyl acrylate), trimethylhexyl dicarbamate, bis(2-hydroxyethyl acrylate) 1,3,3-trimethylcyclohexyl dicarbamate, bis(2-hydroxylethyl acrylate) methylene dicyclohexyl dicarbamate and combinations thereof.

6. The coating composition according to claim 3, wherein ingredient B is independently selected from the group consisting of polyesters, polyurethanes, polyethers and/or alkyd resins each containing at least two pendant ethylenically unsaturated groups each activated by an electron-withdrawing group.

7. The coating composition according to claim 3, wherein ingredient B is independently selected from the group consisting of polyesters, polyurethanes, polyethers and/or alkyd resins each containing at least one pendant acryloyl functional group.

8. The coating composition according to claim 3, further comprising an ingredient D having one or more reactive protons that are more acidic than the two protons of ingredient A, with respect to pKa.

9. The coating composition according to claim 8, wherein the one or more reactive protons of ingredient D are less acidic than the ammonium cation of the ammonium carbamate, with respect to pKa.

10. The coating composition coating composition according to claim 3, further comprising an organic solvent.

11. The coating composition according to claim 10, wherein the organic solvent is independently selected from the group consisting of an alcohol, ester, ether, glycol ether, ketone, aromatic and combinations thereof.

12. The coating composition according to claim 11, wherein the alcohol is independently selected from the group consisting of ethanol, iso-propanol, butanol, iso-butanol, t-butanol and combinations thereof.

13. The coating composition according to claim 3, wherein the catalyst system initiates Michael Addition to achieve crossing linking when the crosslinkable coating composition is applied to a surface.

14. The coating composition according to claim 3, wherein ingredient A, ingredient B and the catalyst system are contained in a container having two or more chambers, which are separated from one another.

15. The coating composition according to claim 14, wherein ingredient A and ingredient B are contained in separate chambers to inhibit any reaction.

16. The coating composition according to claim 14, wherein the catalyst system is contained in the chamber having ingredient A, and optionally containing $CO_2$.

17. The coating composition according to claim 14, wherein ingredient A and ingredient B are contained in the same chamber and the catalyst system is contained in a separate chamber to inhibit any reaction and said separate chamber optionally containing $CO_2$.

18. The coating composition according to claim 3 wherein ingredient A and ingredient B and catalyst system are contained in a container having a single chamber, wherein the container optionally (i) contains $CO_2$.

* * * * *